(12) United States Patent
Larsen et al.

(10) Patent No.: US 7,972,826 B2
(45) Date of Patent: Jul. 5, 2011

(54) METHODS FOR REDUCING ENZYME CONSUMPTION IN SECOND GENERATION BIOETHANOL FERMENTATION IN THE PRESCENCE OF LIGNIN

(75) Inventors: Jan Larsen, Tommerup (DK); Henning Jørgensen, Gentofte (DK)

(73) Assignee: Inbicon A/S, Fredericia (DK)

( * ) Notice: Subject to any disclaimer, the term of this patent is extended or adjusted under 35 U.S.C. 154(b) by 0 days.

(21) Appl. No.: 12/863,601

(22) PCT Filed: Feb. 2, 2009

(86) PCT No.: PCT/IB2009/000172
§ 371 (c)(1),
(2), (4) Date: Jul. 20, 2010

(87) PCT Pub. No.: WO2009/095781
PCT Pub. Date: Aug. 6, 2009

(65) Prior Publication Data
US 2010/0291650 A1    Nov. 18, 2010

Related U.S. Application Data

(60) Provisional application No. 61/025,339, filed on Feb. 1, 2008.

(30) Foreign Application Priority Data

Feb. 1, 2008   (DK) .................................. 2008 00146

(51) Int. Cl.
*C12P 7/10* (2006.01)
*C12Q 1/54* (2006.01)
*C12N 9/42* (2006.01)

(52) U.S. Cl. ........................... 435/165; 435/14; 435/209

(58) Field of Classification Search .................. 435/165, 435/14, 209
See application file for complete search history.

(56) References Cited

U.S. PATENT DOCUMENTS

| 4,409,329 A | 10/1983 | Silver |
| 5,817,212 A | 10/1998 | Jobbins et al. |
| 2003/0124710 A1 | 7/2003 | Borch et al. |

FOREIGN PATENT DOCUMENTS

| WO | WO2005067531 A1 | 7/2005 |
| WO | WO2006056838 A1 | 6/2006 |
| WO | WO2007094643 A1 | 1/2007 |

OTHER PUBLICATIONS

Kristensen et al, Use of surface active additives in enzymatic hydrolysis of wheat straw lignocelluloses, Enzyme and Microbial Technology 40, 2007, 888-895.
Lu et al, Cellulase Absorption and and evaluation of enzyme recycle during hydrolysis and steam-exploded softwood residues, Appl. Biochem and Biotech, vol. 98-100, 2002.
Eriksson et al; mechanism of surfactant effect in enzymatic hydrolysis and lignocelluloses, Enzyme and Microbial Tech, 31, 2002, 353-364.
Börjesson et al, Enhanced enzymatic conversion of softwood lignocelluloses by poly(ethylene glycol) addition, Enzyme and Microbial Tech. 40, 2007, 754-762.
Börjesson et al; Effect of polyethylene glycol on enzymatic hydrolysis and absorption of cellulose enzymes to pretreated lignocelluloses, Enzyme and Microbial technology 41, 2007, 186-195.
Dasari et al: The effect of particle size on hydrolysis reaction rates and rheological properties in cellulosic slurries. Appl. Biochem, and Biotech, vol. 136-140, 2007.
Tabka et al; Enzymatic saccharification of wheat straw for bioethanol production by a combined cellulase xylanase and feruloyl esterase treatment, Enzyme and microbial tech 39, 2006, 897-902.
Lee et al: Effect of surfactants on ethanol fermentation using glucose and cellulosic hydrolyzates, Biotech. Letters, vol. 18(3), 1996, 299-304.
Ballesteros et al; Effect of Surfactants and zeolites on simultaneous saccharification and fermentation of steam-exploded poplar biomass to ethanol, Appl. Biochem. and Biotech, vol. 70-72, 1998.
Alkasrawi et al.; The effect of Tween-20 on simultaneous saccharification and fermentation of softwood to ethanol, Enzyme and Microbial Technology 33 (2003) 71-78.
Helle et al.; Effect of Surfactants on Cellulose Hydrolysis, Biotechnology and Bioengineering 42: 611-617, 1993.
Park et al.; Effects of nonionic surfactant on enzymatic hydrolysis of used newspaper, Biotechnology and Bioengineering 39: 117-120, 1992.
Ooshima et al.; Enhancement of enzymatic hydrolysis of cellulose by surfactant, Biotechnology and Bioengineering 28: 1727-1734, 1986.
Kaya et al.; Influence of surfactants on the enzymatic hydrolysis of xylan and cellulose, Tappi Journal 78:150-157, 1995.
ISA, International Search Report, European Patent Office, 2009.
IPEA, International Preliminary Report on Patentability, European Patent Office, 2010.

*Primary Examiner* — Tekchand Saidha
(74) *Attorney, Agent, or Firm* — Robert C. Casad, Jr.

(57) ABSTRACT

Provided are methods of liquefaction, saccharification and fermentation of pre-treated lignocellulosic biomass in production of bioethanol. Addition of PEG or surfactant is effective to enhance cellulase hydrolysis yields at high dry matter (>20%) at surprisingly low concentrations compared with comparable results in low dry matter hydrolysis. This effect is most pronounced at comparatively low cellulase loading <7 FPU (g DM)$^{-1}$. At high dry matter content, cellulase enzyme consumption can be reduced, without loss of hydrolysis yield, by addition of small quantities of PEG or surfactant.

19 Claims, 6 Drawing Sheets

Figure 1: Effect of PEG/surfactant concentration (Berol 08 and PEG 6000) on cellulose conversion of steam pre-treated wheat straw. Hydrolysis by 5 FPU (g DM)$^{-1}$ for 24 hours. Results are averages of triplicates.

Figure 2: Effect of PEG concentration (PEG 6000) on cellulose conversion of steam pre-treated wheat straw. Hydrolysis by 2.1 FPU (g DM)$^{-1}$ for 24 hours followed by SSF for 120 hours.

Figure 3: Effect of PEG6000 at 0.01 g/g DM as a function of reaction time for -steam pre-treated wheat straw subject to hydrolysis by 7.0 FPU (g DM)$^{-1}$ for 96 hours (squares) or pre-hydrolysed 6 hours by 2.5 FPU (g DM)$^{-1}$ then used directly in SSF for 144 hours (diamonds).

Figure 4: Effect of PEG6000 at 0.01 g/g DM as a function of dry matter content for steam pretreated wheat straw pre-hydrolysed 6 hours by 5.0 FPU (g DM)$^{-1}$ then used directly in SSF for 144 hours.

Figure 5: Effect of 0.01 g PEG/g DM on cellulose conversion of steam pre-treated wheat straw as a function of enzyme loading. Pre-hydrolysis by 2.5 - 10.7 FPU (g DM)$^{-1}$ for 6 hours followed by SSF for 144 hours.

Figure 6: Enhancement of cellulase activity in a SSF process at high dry matter by adding PEG at 0.01 g/g DM. Expressed as a percentage of added enzyme activity at different levels of added enzyme activity.

METHODS FOR REDUCING ENZYME CONSUMPTION IN SECOND GENERATION BIOETHANOL FERMENTATION IN THE PRESCENCE OF LIGNIN

This application is a national stage entry of PCT/IB2009/000172, international filing date Feb. 2, 2009, which claims priority to PA 2008 00146 filed Feb. 1, 2008 and to U.S. provisional application 61/025,339, filed Feb. 1, 2008.

FIELD OF THE INVENTION

The invention relates in general to methods of liquefaction and saccharification of lignocellulosic biomass and to methods of second generation bioethanol fermentation using PEG or surfactants as chemical additives.

BACKGROUND

Lignin content has been an obstacle to efficient transformation of lignocellulosic biomass to bioethanol, feeds, organic precursors and other useful products. Enzymatic conversion of lignocellulosic polysaccharides to fermentable sugars typically requires high enzyme loadings to overcome comparatively low efficiencies of enzymatic catalysis. The comparatively inefficient hydrolysis of cellulosic substrates in pre-treated lignocellulosic biomass is partly due to obstruction by lignin of enzyme access to catalytically productive cellulose binding. The precise nature of this obstruction is not completely understood but apparently arises from the complex and hydrophobic nature of lignin and from its intimate distribution between cellulose fibers.

Part of the deleterious effect of lignin on cellulose hydrolysis in pre-treated lignocellulosic biomass is due to "non-productive" binding of cellulase enzymes to lignin-rich residual material that lacks polysaccharides. See ref. 1. Another aspect is that lignin provides a physical-chemical barrier to catalytically productive enzyme binding with cellulose substrates, further limiting hydrolysis rates. See ref. 2. Lignin-containing pre-treated biomass exhibited roughly equivalent cellulase binding in mg/g substrate compared with de-lignified biomass. However, lignin-containing substrates exhibited much lower initial rates of hydrolysis—lower by a factor of at least three from hydrolysis rates achieved with de-lignified substrates. This reduction in hydrolysis rates could not be explained solely by "non-productive" enzyme binding to lignin. Some additional "lignin barrier" to enzyme access was clearly implicated. The precise nature of this "lignin barrier" remains unclear. Catalytically productive binding of cellulase enzymes to cellulosic substrates has been studied in detail and is known to involve physical-chemical subtleties. Lu et al (ref 2) suggest that "re-swelling" properties of cellulose fibers in water have some influence on cellulose structure, enzyme adsorption capacity and enzymatic hydrolysis by cellulases. A functional effect of cellulose fiber "swelling properties" is suggested by the much higher cellulase binding exhibited by pre-treated lignocellosic substrates (both lignin containing and de-lignified) compared with pure microcrystalline cellulose (AVICEL™), which is produced by processes involving drying and bleaching. Further, amorphous regions of cellulose fibers provide greater opportunities for catalytically productive cellulase binding compared with crystalline regions of cellulose fibers. See e.g ref. 3 and 4.

One approach to reducing deleterious effects of lignin has been de-lignification of pre-treated lignocellulosic biomass. See e.g ref. 5 and 6. Another approach to the lignin problem which has been explored on an experimental scale has been introduction of additives to hydrolysis mixtures, including surfactants, proteins and other lignin-binding polymers. In particular, polyethylene glycol (PEG) of varying molecular weights has shown promise. Most of the surfactants tested previously were similar to PEG in that they included ethylene oxide core structures, such as TWEEN™. See ref. 7, 8, 9, 10 and 11.

Efforts to "scale up" the use of "lignin binding" additives from an experimental scale to production scale have focused on the study of molecular mechanisms of the surfactant/PEG effect on cellulose hydrolysis rates. See ref. 12 and ref. 13. Börjesson et al confirmed the conclusions of previous studies by Sewalt et al (1997) (ref. 7) and by Erikkson et al (2002) (ref. 10) that the surfactant/PEG effect primarily involves reversal of catalytically unproductive enzyme binding to lignin. Börjesson et al note that this conclusion is consistent with observations of effects comparable to the PEG effect achieved by addition of bovine serum albumin, which is widely used to suppress non-specific protein binding in various experimental contexts. See ref. 14.

With the express aim of identifying optimal conditions for PEG/surfactant addition, Börjesson et al. studied the surfactant/PEG effect in close detail, including binding isotherms of PEG 4000 with steam pre-treated spruce. Börjesson et al. concluded that optimal PEG conditions could be achieved by addition of about 0.05 g PEG (g DM)$^{-1}$. These optimal PEG conditions are in good agreement with results reported by other researchers. Ref. 15 reports that optimal hydrolysis conditions could be achieved using steam and acid pre-treated corn stover by addition of about 0.1 g (g DM)$^{-1}$ of non-ionic, ethylene oxide polymer surfactants selected from the group consisting of SOFTANOL™ 50, SOFTANOL™ 90, SOFTANOL™ 120, SOFTANOL™ 200, LUTSENOL™ AT50, LUTSENOL™ AT80, TERGITOL™ NP9, NOVELL II™ TDA 6.6, NOVELL II™ TDA 8.5, BRIJ™ 35, BRIJ™ 56, BRIJ™ 97, BRIJ™ 98, and PLURONIC™ F68. Ref. 16 reports that optimal hydrolysis conditions could be achieved using wheat straw pre-treated by water and by sulfuric acid by addition of about 0.05 g (g DM)$^{-1}$ of either BEROL™ 08, PEG 6000, TWEEN™ 80 or BSA. Ref. 10 reports hydrolysis conditions using steam treated spruce with about 0.05 g (g DM)$^{-1}$ of non-ionic surfactants including TWEEN™ 20, TWEEN™ 80, TRITON™ X-100, TRITON™ X-114, AGRIMUL™ NRE 1205, and hydrophobically modified ethylene oxide co-polymer. Ref. 17 reports hydrolysis using steam exploded wheat straw with about 0.05 g (g DM)$^{-1}$ of TWEEN™ 20.

Here we report the surprising discovery that, when hydrolysis of pre-treated lignocellulosic biomass is conducted at high dry matter content, above 20%, optimal PEG/surfactant conditions can be achieved at lower levels than those known in the prior art, or about 0.025 g (g DM)$^{-1}$. The lowered optimal PEG/surfactant conditions enables cost-saving reductions in consumption of additives in bioethanol production at high dry matter content. Even sub-optimal PEG/surfactant conditions, as low as 0.01 g (g DM)$^{-1}$, provide satisfactory results at high dry matter. An immediate implication of this result is that the molecular mechanism of the PEG/surfactant effect is likely not a simple matter of competitive inhibition of catalytically non-productive lignin binding, but rather involves potentially intricate details of inter-fiber surface chemistry.

We further report that this effect is most pronounced at comparatively low cellulose loadings, <7 FPU (g DM)$^{-1}$. Thus, hydrolysis yields can be improved and enzyme requirements reduced at high dry matter by adding surprisingly small quantities of PEG or surfactant.

Hydrolysis mixtures prepared using high dry matter content, in the presence of PEG/surfactant, can be readily used in simultaneous saccharification and fermentation (SSF) and other processes involving fermentation in the presence of lignin.

SUMMARY OF THE INVENTION

In some embodiments, the invention provides processes for liquefaction and saccharification of pre-treated lignocellulosic biomass whereby enzymatic hydrolysis is conducted at high dry matter content, >20%, in the presence of a surfactant or PEG, preferably at optimal or sub-optimal concentrations, where optimal concentrations are about 0.025 g (g DM)$^{-1}$. Sub-optimal concentrations as low as 0.01 g (g DM)$^{-1}$ provide effective improvement of hydrolysis yield at high dry matter using low cellulase loadings <7 FPU (g DM)$^{-1}$.

In other embodiments, the invention provides methods of fermentation of bioethanol using pre-treated lignocellulosic biomass hydrolysed at high dry matter content in the presence of a surfactant or PEG.

DETAILED DESCRIPTION OF PREFERRED EMBODIMENTS

As used herein the following terms have the following meanings, (i). Solid Fraction of a Pre-Treated Lignocellulosic Biomass Lignocellulosic biomass refers to material derived from plants or other organisms in which carbohydrate content is substantially cellulose and hemicellulose and which comprises more than 5% lignin. Lignin is a complex aromatic network formed by polymerisation of phenyl propane and comprising monomers including: p-coumaryl alcohol, coniferyl alcohol and sinapyl alcohol, typically linked through arylglyceryl-β-aryl ether bonds. The term as used herein includes processed materials, such as papers having more than 5% lignin, as well as primarily natural materials, such as agricultural wastes. Lignocellulosic biomass will typically comprise water content. A mixture of water and/or other agents and/or solvents comprising lignocellulosic biomass as the predominant solid component can also be referred to as "a" lignocellulosic biomass within the meaning of the term as used. The carbohydrate composition of a lignocellulosic biomass may be changed during pre-treatment. Pre-treatment refers to a manipulation of lignocellulosic biomass that renders its cellulosic component more accessible to enzymes that convert carbohydrate polymers into fermentable sugars. Initially "pre-treated" refers to a lignocellulosic biomass that has been subjected to at least one pre-treatment. The solid fraction of a pre-treated lignocellulosic biomass refers to insoluble materials, primarily fibers, obtained from pre-treatment of biomass. Typically a liquid fraction will also be obtained, which contains soluble cellulose derivatives, sugars and other molecules. The term as used refers to all or part of a solid fraction obtained from pre-treatment of lignocellulosic biomass.

(ii). Effective Amount of One or More Cellulytic Enzymes

An amount of cellulytic enzyme is effective where, under conditions used, cellulosic substrates are hydrolysed to sugar yields of at least about 50% theoretical yield. One or more cellulytic enzymes may be combined in any ratios to provide a collectively effective amount.

(iii). Hydrolysis Mixture

Refers to a mixture of the solid fraction of a pre-treated lignocellulosic biomass with cellulytic enzymes and/or other additives. The term also may refer to a simultaneous saccharification and fermentation (SSF) process. Hydrolysis mixtures may be provided in batch modes or in continuous or semi-continuous processes.

(iv). Dry Matter

Dry matter refers to insoluble material. Typically, dry matter comprises insoluble fibers obtained from the solid fraction of a pre-treated lignocellulosic biomass.

We have discovered that, surprisingly, using high dry matter content (>20%), optimal conditions for enzymatic hydrolysis of pre-treated lignocellulosic biomass can be achieved using much smaller quantities of surfactants or PEG than were previously considered feasible. In particular, levels of PEG as low as 0.01 g (g DM)$^{-1}$ can provide substantial improvements of hydrolysis yields at high dry matter (insoluble fiber).

The molecular mechanisms of this remarkable effect are not yet clear. Previously, the effect of surfactant in cellulose hydrolysis has been attributed primarily to essentially competitive reversal of catalytically non-productive enzyme binding to lignocellulose surfaces. This "high dry matter effect" appears to involve some other processes which are not immediately obvious.

Some contribution may arise from subtle hydration effects involving PEG or surfactants bound at the cellulose surface. Such effects would be exaggerated in hydrolysis at high dry matter content, where essentially all of the aqueous content exists within cellulose fibers. In contrast, at low dry matter content, a greater volume of water exists between cellulose fibers.

Peculiar surface hydration effects have been identified in previous studies. PEG in particular has been widely used as a surface coating to resist non-specific protein binding. See for review ref. 18. The molecular mechanisms of PEG/protein repulsion are believed to include a variety of subtle physical-chemical effects at the interaction surface, most notably including effects involving hydration water structure.

Another factor which may contribute to the "high dry matter effect" is different fiber swelling properties at high dry matter, compared with the swelling properties of fully "immersed" fibers in low dry matter hydrolysis.

One factor which does not appear to contribute to the effect is the mechanical disruption of fibers which occurs during high dry matter hydrolysis in gravity mixers, as described in WO2006/056838 (ref. 19). Smaller particle sizes generally provide better hydrolysis yields. See e.g. ref. 20. However, the enhancement of hydrolysis yields by PEG or surfactant is unaffected by milling or other mechanical disruption of feed stocks to achieve smaller particle size.

In some embodiments, the invention provides a process for liquefaction and saccharification of lignocellulosic biomass comprising the steps of provividing the solid fraction of a pre-treated lignocellulosic biomass, and treating said solid fraction with an effective amount of one or more cellulytic enzymes in the presence of a surfactant or PEG;

wherein the hydrolysis mixture comprises >20% dry matter.

Any suitable lignocellulosic biomass feedstock having lignin content of at least about 10% may be used including at least corn stover, wheat straw, rice straw, bagasse, corn fiber, hardwood bulk, softwood bulk, nut shells, corn cobs, grasses, including coastal Bermuda grass and switch grass, paper, including newspaper, waste papers and paper from chemical pulps, sorted refuse, cotton seed hairs, and other materials well known in the art.

In preferred embodiments, the solid fraction of a lignocellulosic biomass used to practice methods of the invention comprises at least about 2.5 kg, or at least about 100 kg, or at least about 500 kg, or at least about 1000 kg.

Lignocellulosic biomass feedstocks may be pre-treated and processed by any suitable method that provides separation into at least a liquid fraction and a solid fraction comprising fibers having lignin content of at least about 10%. Preferably, feed stocks are pre-treated by the methods described in WO 2007/009463 (ref. 21), which is hereby expressly incorporated by reference in entirety. Other suitable pre-treatment methods include variants of steam explosion, high pressure steam, liquid hot water, dilute acid, ammonia fiber explosion, wet oxidation and physical treatments such as milling. Many suitable variants of these methods and other methods of pre-treatment are well known in the art.

Separation of a liquid fraction from a solid fraction of pre-treated biomass may be achieved by a variety of means. Preferably, pre-treated biomass is subject to washing and pressing-steps. Alternatively, for example, in hot water pre-treatment methods, a suitable solid fraction may be produced directly.

Enzymatic hydrolysis mixtures can be prepared by a variety of methods using the solid fraction of a pre-treated lignocellulosic biomass. In preferred embodiments, pre-treated biomass is subject to pre-hydrolysis for 2-24 hours, prior to introduction of fermentative organisms, optionally involving transfer to a separate vessel, for a simultaneous saccharification and fermentation (SSF) process. In preferred embodiments, enzymatic hydrolysis may be conducted under controlled pH, temperature and mixing conditions using any of the methods for attaining high dry matter content (>20%) in enzymatic liquefaction and saccharification of pre-treated lignocellulosic biomass discussed in WO2006/056838, which is hereby expressly incorporated by reference in entirety. In some embodiments, the solid fraction of a pre-treated lignocellulosic biomass may be hydrolysed in an essentially batch manner, or, alternatively, may be processed in an essentially continuous or semi-continuous manner. In some embodiments, pre-treated biomass can be introduced in a relatively continuous "production line" manner to pre-hydrolysis in a pre-hydrolysis unit, which provides means for conveying biomass further into a communicating fermentation unit for SSF. Alternatively, pre-treated lignocellulosic biomass may be used directly in an SSF process without pre-hydrolysis.

Enzymes suitable for practice of enzymatic hydrolysis in some embodiments are, preferably, cellulases. Suitable cellulases include, at least, CELLUCLAST™ (available from Novozymes NS) and NOVOZYM™ 188 (available from Novozymes NS). Other commercially available preparations may be used including CELLUZYME™, CEREFLO™ and ULTRAFLO™ (Novozymes A/S), ACCELLERASE™ 1000, LAMINEX™ and SPEZYME™ CP (Genencor Int.), and ROHAMENT™ 7069 W (Rohm GmbH). Other cellulytic enzymes are also suitable including any enzyme involved in the degradation of lignocellulose to glucose, xylose, mannose, galactose, and arabinose, including endoglucanases, cellobiohydrolases, glucohydrolases, β-glucosidases, xylanase and other hemicellulases, or any combination thereof. Surprisingly, PEG or surfactants are also effective at very low concentrations in enhancing xylanase activity at high dry matter content (>20%). Suitable cellulolytic enzymes may hydrolyze cellulose in the acid, neutral, or alkaline pH-range. A suitable cellulase(s) or other cellulolytic enzyme(s) may be of fungal or bacterial origin, obtainable or isolated and purified from microorganisms known to be capable of producing cellulolytic enzymes. Alternatively, the cellulase(s) or other cellulytic enzyme(s) may be genetically engineered and expressed in fermentative or other microorganisms, derived from fungal, bacterial, chimeric or artificial sequences or any combination thereof. Suitable cellulolytic enzymes may be produced by methods well known in the art or by new methods developed in future.

Cellulase activity, hydrolysis of 1,4 β-D-glycosidic linkages in cellulose, can be determined by standard biomass Laboratory Analytical Procedure #006, "Measurement of cellulase activity," ref. 22. The method describes a procedure for measurement of cellulase activity in terms of "filter-paper units" (FPU) per milliliter of original (undiluted) enzyme solution. Alternatively, cellulase activity in terms of "filter-paper units" can be measured by the method described in ref. 23.

Endoglucanase activity, endohydrolysis of 1,4 β-D-glycosidic linkages in cellulose and other substrates, endoglucanase activity can be determined using carboxymethyl cellulose (CIVIC) hydrolysis according to the procedure of ref. 23.

Cellobiohydrolase activity, hydrolysis of 1,4 β-D glucosidic linkages in cellulose and other substrates, can be determined by the method of ref. 24.

Glucohydrolase activity, hydrolysis of 1,4-linkages (O glycosyl bonds) in cellulose and other substrates, can be determined by the method of ref. 25.

β-glucosidase activity, hydrolysis of terminal non-reducing β-D-glucose residues with release of β-D-glucose from a variety of substrates, can be determined by the method of ref. 26.

Xylanase activity, hydrolysis of 1,4 β-D-xylosidic linkages in xylans, can be determined as nkat by the method of ref. 27.

An amount of cellulytic enzyme that is "effective" for hydrolysis of any given lignocellulosic feed stock subject to any given pre-treatment method and post pre-treatment processing depends on a number of variables, including temperature, reaction time, pH, and dry matter content. Practical considerations or cost balancing may dictate constraints on reaction time. Reaction temperature is typically controlled to optima for specific enzyme activities. However, other considerations may also apply, for example in SSF processes, temperature optima for fermentative organisms are typically lower than temperature optima for cellulytic enzymes. In the particular case of xylanase activity, an effective amount of xylanase is an amount where, under the conditions used, xylanase conversion is at least 20% theoretical yield, including enhancement of hydrolysis by PEG. In general, to achieve adequate hydrolysis yields in shorter times requires greater amounts of cellulytic enzymes. Different enzymes and different batches of the same enzyme preparation may have different levels of specific activity. An amount of cellulytic enzyme added to a hydrolysis mixture and/or an SSF process can be expressed as a unit of activity per gram dry matter. For example, cellulase activity added can be expressed as FPU (g DM)$^{-1}$. An amount of cellulytic enzyme is effective where, under conditions used, cellulosic substrates are hydrolysed to sugar yields of at least about 50% theoretical yield, including enhancement of hydrolysis yield by addition of PEG or surfactant. One or more cellulytic enzymes may be combined in any ratios to provide a collectively effective amount.

In preferred embodiments, cellulytic enzymes are added in amounts between about 3-6 FPU (g DM)$^{-1}$.

In preferred embodiments, PEG is added to the hydrolysis mixture in amounts ranging from about 0.005 to about 0.025 g (g DM)$^{-1}$, preferably about 0.01 g (g DM)$^{-1}$, or between 0.01 and 0.015 g (g DM)$^{-1}$, or between 0.01 and 0.020 g (g DM)$^{-1}$. PEG of any molecular weight may be used in practice of some embodiments of the invention. Most preferable is PEG 6000 or a combination of PEG 6000 and PEG 1500. Comparative tests could not identify any molecular weight trend amongst PEGs and demonstrated that PEG 1500, 2000, and 4000 were essentially equally effective alternatives when added in the same amounts in g (g DM)$^{-1}$. Optimum PEG concentrations for improved hydrolysis yields can be achieved in high dry matter conditions at about 0.025 g (g DM)$^{-1}$. However, optimum PEG concentrations from a cost perspective may be achieved at lower levels.

In preferred embodiments, the concentration of PEG or surfactant used is about 0.025 g (g DM)$^{-1}$ or less, wherein no improvement of hydrolysis yield can be achieved over 0.025 g (g DM)$^{-1}$ by increasing the concentration to 0.05 g (g DM)$^{-1}$.

In other preferred embodiments, the concentration of PEG or surfactant is about 0.01 g (g DM)$^{-1}$ wherein the absolute improvement in hydrolysis yield is at least about 10%.

As used herein, the term "about" as used in reference to a concentration of PEG or surfactant, to an enzyme activity, or to a quantity of mass means +/−15%. The term about as used in reference to a % improvement in hydrolysis yield refers to normal rounding. All numerical values as used herein are qualified by the term about. While unsubstituted PEG itself is not a surfactant per se, enhancement of hydrolysis yields by PEG are comparable to enhancements achieved by surfactants added in comparable amounts in g (g DM)$^{-1}$. The PEG/surfactant effects are considered to involve the same underlying molecular mechanisms. Accordingly, surfactants may also be used to practice some embodiments. In particular, surfactants containing ethylene oxide chains may be used. Alternatively, non ethylene oxide containing surfactants such as n-decanoyl-n-methyl-D-glucamine may be used. In hydrolysis under low dry matter conditions, optimal concentrations of some surfactants, such as TWEEN™ 20 were previously shown to be about 0.05 g (g DM)$^{-1}$, that is, identical with PEG. However, other surfactants exhibited slightly higher optimal concentrations. For example, SOFTANOC 90 was reportedly optimal under low dry matter conditions at about 0.1 g (g DM)$^{-1}$. See ref. 15. As with PEGs, surfactants may be added in amounts that are technically sub-optimal, yet preferred in terms of cost savings. Any suitable surfactant may be used to practice some embodiments at optimal concentrations about 50% of those observed in low dry matter conditions. Any of the surfactants discussed in WO2005/067531 (ref. 15), which is hereby expressly incorporated by reference in entirety, may be used at concentrations of about 0.05 g(g DM)$^{-1}$ or less including but not limited to: SOFTANOL™ 50, SOFTANOL™ 90, SOFTANOL™ 120, SOFTANOL™ 200, LUTENSOL™ AT50, LUTENSOL™ AT80, TERGITOL™ NP-9, NOVELL II™ TDA 6.6, NOVELL II™ TDA 8.5, BRIJ™ 35, BRIJ™ 56, BRIJ™ 97, BRIJ™ 98. Other suitable surfactants include any of the TWEEN™ series, TRITON™ series, EMULGEN™ series, BRIJ™ series, LUTENSOL™ series, TERGITOL™ series, NOVELL™ series.

EXAMPLES

Example 1

Optimization of PEG Concentration at Low DM Dontent (5% Insoluble Fiber)

Cut wheat straw (average particle size of approximately 40 mm) was continuously pre-treated by steam at 185-200° C. for 10-15 minutes. The pre-treatment must ensure that the structure of the lignocellulosic content is rendered accessible to the enzymes, and at the same time the concentrations of harmful inhibitory by-products such as acetic acid, furfural and hydroxymethyl furfural remain substantially low. Therefore a part of the pre-treatment is a washing and pressing step, where the pre-treated straw is washed by water or condensate. After washing and pressing the cellulosic fibres leave the pre-treatment at a dry matter content of app. 25-35%. The pre-treated straw was collected in plastic bags and stored at −20° C. until use.

The pre-treated straw was dried at 35° C. for 1-2 days and then cut and strained through a 1.5 mm sieve on a RETSCH™ SM 2000 cutting mill. The hydrolysis was performed using an enzyme mixture of CELLUCLAST™ 1.5 I and NOVOZYM™ 188 (weight ratio 5:1, from Novozymes NS, Bagsvaerd, Denmark) with a filter paper activity of 74 FPU g$^{-1}$, as measured by the filter paper assay.

The hydrolysis was performed in 50 ml Falcon tubes (total reaction volume 40 g), at 5% DM (w/w) in a 50 mM sodium citrate buffer pH 4.80 and using an enzyme loading of 5 FPU (g DM)$^{-1}$. In the concentration effect study, BEROL™ 08 was tested at 0.005, 0.025, 0.05 and 0.10 g (g DM)$^{-1}$, and PEG 6000 was tested at 0.005, 0.01, 0.025 and 0.05 g (g DM)$^{-1}$. The test tubes where placed in a heated (50° C.), shaking water bath (80 rpm) for 24 h. All experiments were performed in triplicate. Samples for sugar analysis were boiled for 10 min to terminate the reaction and stored at −20° C. until analysis.

Figure 1:
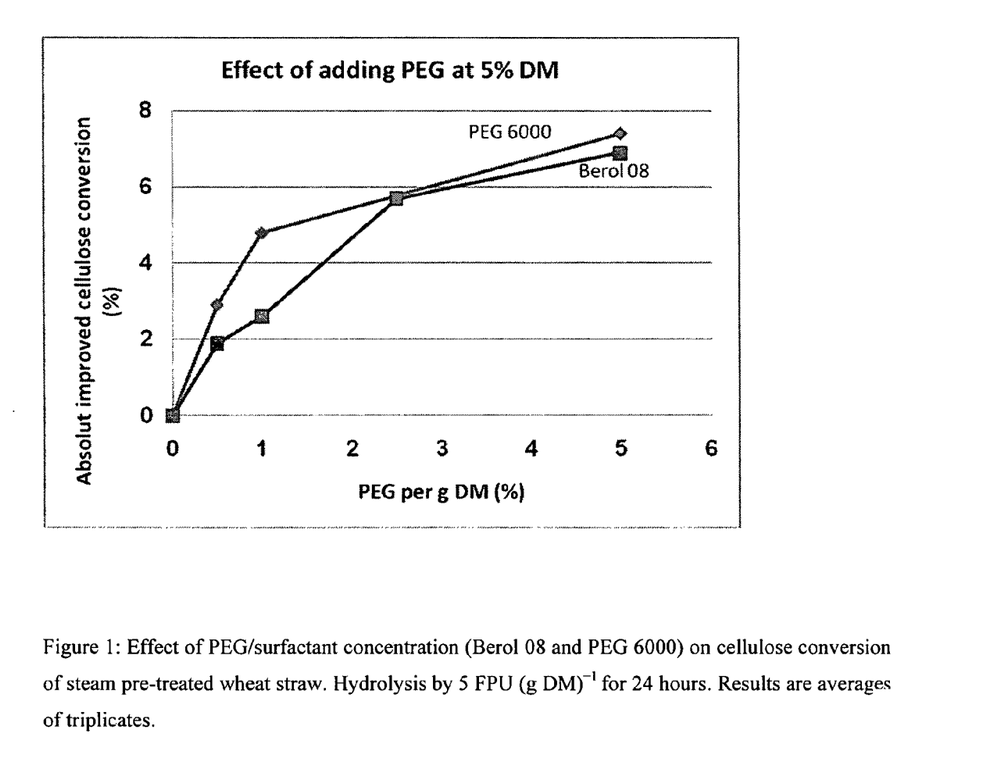
FIG. 1 shows optimisation of PEG and BEROL™ 08 concentration in cellulose hydrolysis at low dry matter content (5% insoluble DM).

The correlation between amount of PEG/surfactant added and effect on hydrolysis was investigated for BEROL™ 08 and PEG 6000 on pre-treated wheat straw (FIG. 1). Improvements in cellulose conversion are expressed in absolute terms—i.e., net improvement in % theoretical yield. For both PEG and BEROL™ 08, the effect on cellulose hydrolysis of increasing PEG/surfactant concentration leveled off above 0.025 g (g DM)$^{-1}$. The optimum ratio between PEG/surfactant and substrate was about 0.05 g (g DM)$^{-1}$. The difference between BEROL™ 08 and PEG 6000 at optimum levels was negligible.

Example 2

Optimization of PEG Dose at High DM Content (25% Insoluble DM)

Cut wheat straw (average particle size of approximately 40 mm) was continuously pre-treated by steam at 185-200° C.

for 10-15 minutes. The pre-treatment must ensure that the structure of the lignocellulosic content is rendered accessible to the enzymes, and at the same time the concentrations of harmful inhibitory by-products such as acetic acid, furfural and hydroxymethyl furfural remain substantially low. Therefore a part of the pre-treatment is a washing and pressing step, where the pre-treated straw is washed by water or condensate. After washing and pressing the cellulosic fibres leave the pre-treatment at a dry matter content of app. 25% (insoluble DM). The fibres, about 2.5 kg dry matter, were pre-hydrolysed by means of NOVOZYM™ 188 and CELLUCLAST™ 1.5 FG at 50° C. using an enzyme loading of 2.1 FPU (g DM)$^{-1}$. Afterwards simultaneous saccharified and fermented (SSF) at 30-33° C. with common bakers yeast (Baker's yeast, De Danske Spritfabrikker). In this concentration effect study, PEG 6000 was tested at 0.005, 0.01, 0.025 and 0.05 g (g DM)$^{-1}$.

The pre-hydrolysis and SSF was conducted in a free fall mixer (according to the methods described in WO2006/056838). Pre-hydrolysis at 50-55° C. for 24 hours, and SSF at 33° C. for 120 hours.

Figure 2:
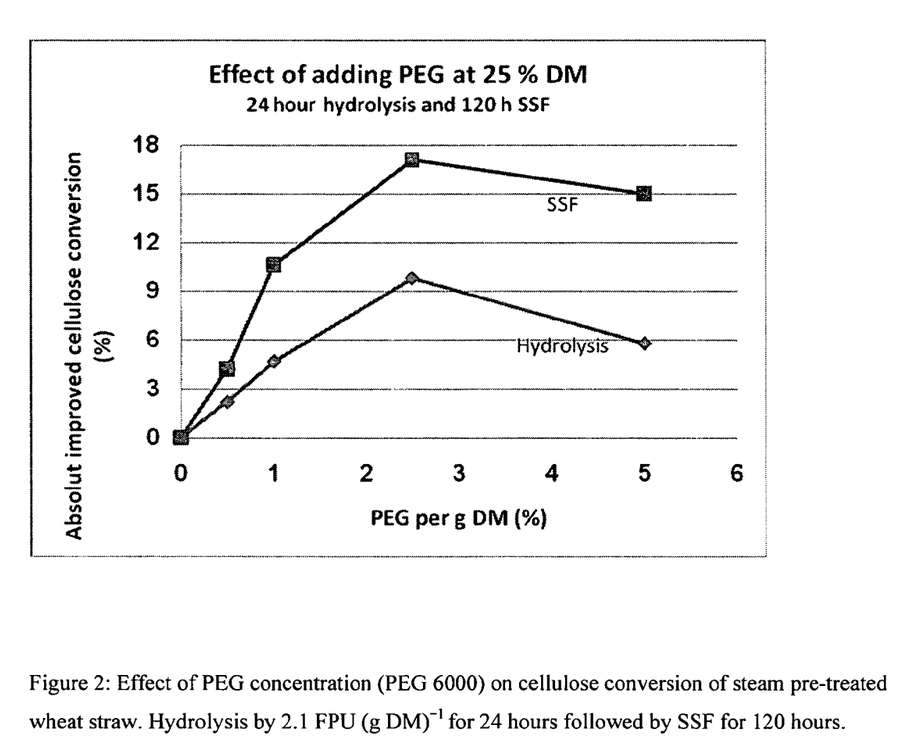
FIG. 2 shows optimisation of PEG concentration in cellulose hydrolysis and in SSF at high dry matter contents (25% insoluble DM).

The correlation between amount of PEG added and effect on hydrolysis was investigated for PEG 6000 on pre-treated wheat straw, both in pre-hydrolysis at low enzyme concentration and also in subsequent SSF (FIG. 2). As shown, the effect on cellulose hydrolysis of increasing PEG concentration was diminished above 0.025 g (g DM)$^{-1}$. The optimum ratio between surfactant and substrate was about 0.025 g (g DM)$^{-1}$.

Notably, the effect of PEG is more pronounced in SSF than in hydrolysis alone.

Example 3

Effect of 0.01 g PEG (g DM)$^{-1}$ as a Function of Time (26-30% Insoluble DM)

Cut wheat straw (average particle size of approximately 40 mm) was continuously pre-treated by steam at 185-200° C. for 10-15 minutes then washed and pressed to dry matter content of app. 26-30% (insoluble DM). In one experiment, fibres, about 2.5 kg dry matter, were hydrolysed 96 hours by means of NOVOZYM™ 188 and CELLUCLAST™ 1.5 FG at 50° C. using an enzyme loading of 7.0 FPU (g DM)$^{-1}$ in the presence of PEG 6000 at 0.01 g(g DM)$^{-1}$. In a comparative experiment, fibers were subject to 6 hours pre-hydrolysis using NOVOZYM™ 188 and CELLUCLAST™ 1.5 FG at 50° C. using an enzyme loading of 2.1 FPU (g DM)$^{-1}$ then simultaneously saccharified and fermented (SSF) 144 hours at 30-33° C. with common bakers yeast (Baker's yeast, De Danske Spriffabrikker) in the presence of PEG6000 at 0.01 g (g DM)$^{-1}$.

Hydrolysis and SSF was conducted in a free fall mixer (according to the methods described in WO2006/056838).

Figure 3:
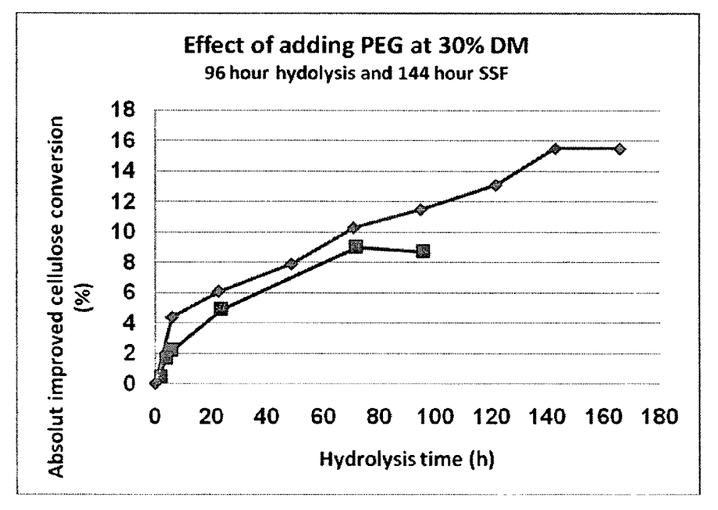
FIG. 3 shows effect of PEG at 0.01 g (g DM)$^{-1}$ as a function of time in cellulose hydrolysis and in SSF at high dry matter content (26-30% insoluble DM).

FIG. 3 shows improvement in cellulose conversion as a function of reaction time for hydrolysis (squares) and SSF (diamonds). Improvements are expressed in absolute terms—i.e. net improvement in % theoretical yield at specified time points. Total conversion of cellulose was equivalent in both experiments—about 60% of cellulose was converted into glucose/ethanol. However the improvement in yield from added PEG is greater in SSF than in hydrolysis alone. The increased enhancement in SSF cannot be explained by the lower temperatures used in SSF—the PEG effect is increased at higher temperatures. See ref. 12.

Example 4

Effect of 0.01 g PEG (g DM)$^{-1}$ at Different DM Contents in SSF Process (6-26% Insoluble DM)

Figure 4:
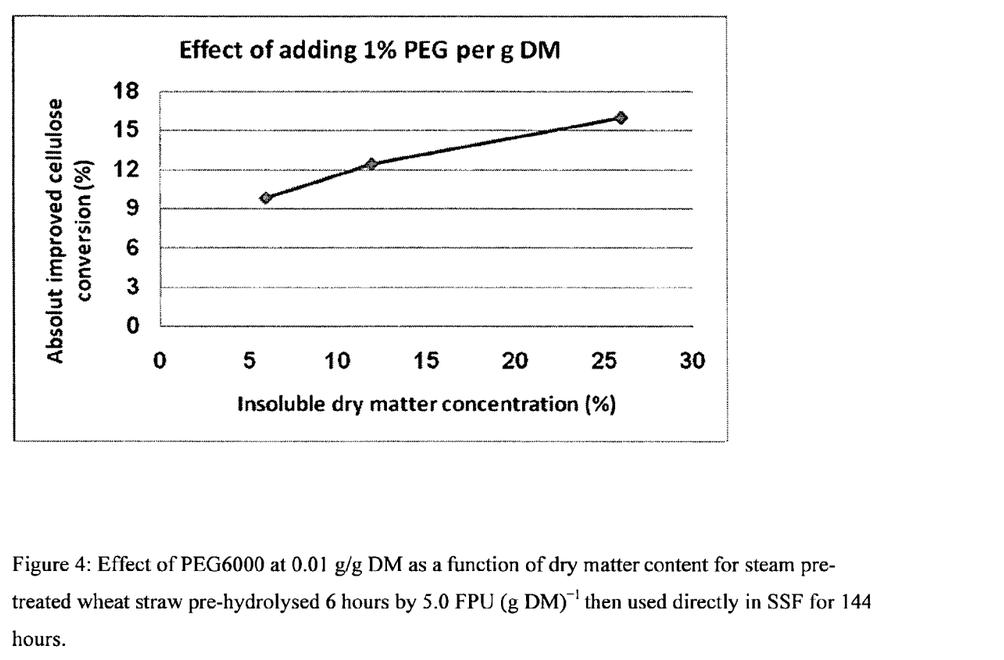
FIG. 4 shows effect of PEG at 0.01 g (g DM)$^{-1}$ in pre-hydrolysis followed by SSF at different dry matter contents (from 6% to 26% insoluble DM).

Cut wheat straw (average particle size of approximately 40 mm) was continuously pre-treated by steam at 185-200° C. for 10-15 minutes then washed and pressed to different dry matter content of app. 26% (insoluble DM). Solid fractions comprising different dry matter contents were pre-hydrolysed 6 hours with NOVOZYM™ 188 and CELLUCLAST™ 1.5 FG at 50° C. using an enzyme loading of 5.0 FPU (g DM)$^{-1}$ then simultaneously saccharified and fermented (SSF) 144 hours at 30-33° C. with common bakers yeast (Baker's yeast, De Danske Spritfabrikker) in the presence or absence of PEG 6000 at 0.01 g (g DM)$^{-1}$. Experiments of 26% DM, about 2.5 kg dry matter, were conducted in a free fall mixer (according to the methods described in WO2006/056838). Experiments at 6 and 12% DM were conducted in shake flasks. Dilution from 26% DM to 6 and 12% DM was performed with an acetic acid buffer. FIG. 4 shows improvements in cellulose conversion by addition of PEG at different dry matter conditions. Improvements are expressed in absolute terms—i.e., net improvement in % theoretical yield. As shown, the effect of PEG at 0.01 g (g DM)$^{-1}$ is more pronounced—nearly twofold—at high dry matter content (26% insolubleDM) compared with the effect at low dry matter conditions (5% insolubleDM).

Example 5

Effect of 0.01 g PEG (g DM)$^{-1}$ at Different Enzyme Loadings (26% Insoluble DM)

Figure 5:
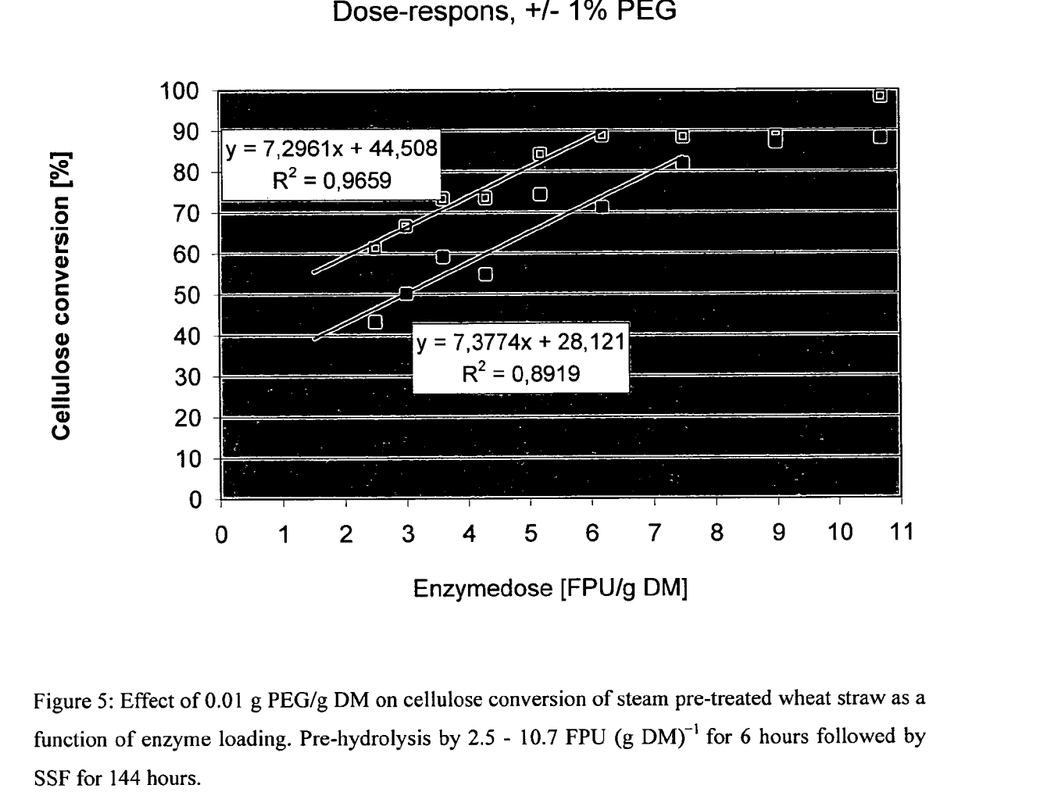
FIG. 5 shows effect of PEG at 0.01 g (g DM)$^{-1}$ in hydrolysis at high dry matter content (26% insoluble DM).
Figure 6:
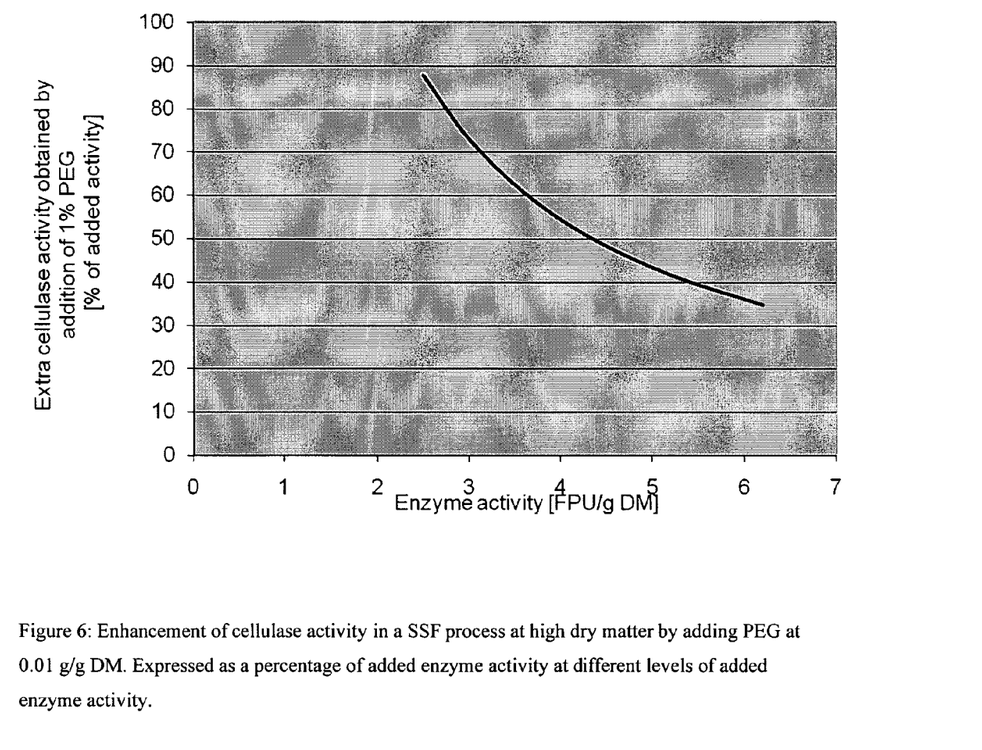
FIG. 6 shows enhancement of cellulase yields at high dry matter by PEG 0.01 g (g DM)$^{-1}$ at different levels of added enzyme activity.

Cut wheat straw (average particle size of approximately 40 mm) was continuously pre-treated by steam at 185-200° C. for 10-15 minutes then washed and pressed to dry matter content of app. 26% (insoluble DM). The fiber fraction, about 2.5 kg dry matter, was hydrolysed 6 hours with NOVOZYM™ 188 and CELLUCLAST™ 1.5 FG at 50° C. using an enzyme loading ranging from 2.5 to 10.7 FPU (g DM)$^{-1}$ then simultaneously saccharified and fermented (SSF) 144 hours at 30-33° C. with common bakers yeast (Baker's yeast, De Danske Spritfabrikker) in the presence or absence of PEG6000 at 0.01 g (g DM)$^{-1}$. Hydrolysis was conducted in a free fall mixer (according to the methods described in WO2006/056838). FIG. 5 shows % cellulose conversion for high dry matter content hydrolysis in the presence (open squares) or absence (solid squares) of PEG at 0.01 g (g DM)$^{-1}$ at different enzyme loadings. As shown, the absolute improved cellulose conversion is about 16% over the range from 2-6 FPU (g DM).$^{-1}$ Above 6 FPU, the effect levels off. The result demonstrates that, depending on severity used in pre-treatment, savings of between 25 and 45% of enzyme loading can be achieved by adding PEG at 0.01 g (g DM)$^{-1}$ in a high dry matter SSF process. Enzymes are a primary expense in bioethanol production. At current price levels for enzymes and PEG, the expense of adding 0.01 g PEG (g DM)$^{-1}$ will likely be offset by enzyme reduction between 10 and 20%. FIG. 6 shows PEG-enhancement of hydrolysis yield expressed as a percentage of added enzyme activity. As shown, savings of greater than 20% can be achieved across the range of enzyme activities tested.

Example 6

Effect of PEG 6000 on Xylan Conversion

Cut wheat straw (average particle size of approximately 40 mm) was continuously pre-treated by steam at 185-200° C.

for 10-15 minutes. The pre-treatment must ensure that the structure of the lignocellulosic content is rendered accessible to the enzymes, and at the same time the concentrations of harmful inhibitory by-products such as acetic acid, furfural and hydroxymethyl furfural remain substantially low. Therefore a part of the pre-treatment is a washing and pressing step, where the pre-treated straw is washed by water or condensate. After washing and pressing the cellulosic fibres leave the pre-treatment at a dry matter content of app. 25-35%.

The hydrolysis was performed in 100 ml plastic bottles (total reaction volume 50 g), at 25% DM (w/w) in a 50 mM sodium citrate buffer pH 4.80 and using an enzyme loading of 2.5 or 5 FPU (g DM)$^{-1}$ of NOVOZY™ 188 and CELLUCLAST™ 1.5 FG L in a 5:1 ratio. This mixture had a xylanase activity of 460 nkat (FPU)$^{-1}$. PEG 6000 was added in the concentrations of 0.0, 0.01 or 0.02 g (g DM)$^{-1}$. The bottles were placed in a heated (50° C.), horizontally placed drum, rotating at 60 rpm, for 72 hours. The 80 cm diameter drum was equipped with two inside paddles that lifted and dropped the plastic bottles during rotation thereby ensuring efficient mixing of the content of the bottles. All experiments were performed in triplicate.

At a xylanase loading of 2300 nkat (g DM)$^{-1}$ addition of 0.01 g (g DM)$^{-1}$ of PEG 6000 improved xylan conversion (measured as release of xylose) by 2% in absolute terms, i.e., net improvement in % theoretical conversion (from 39% without PEG to 41% with PEG). Increasing the PEG 6000 concentration to 0.02 g (g DM)$^{-1}$ provided 3% absolute improvement in xylan conversion relative to xylan conversion without PEG addition (from 36% to 40% theoretical conversion).

At a xylanase loading of 1100 nkat (g DM)$^{-1}$, addition of 0.01 g (g DM)$^{-1}$ of PEG 6000 improved absolute xylan conversion by 4% (from 24% to 28% theoretical conversion).

As shown, PEG is also effective in enhancing xylanase yields in high dry matter hydrolysis, with a more pronounced effect at low enzyme loadings on the order of 1100 nkat (g DM)$^{-1}$ of xylanase activity). Xylanase activity could preferably be used at between 1000-5000 nkat (g DM)$^{-1}$.

The embodiments and examples described here are representative only and not intended to limit the scope of the invention as claimed.

REFERENCES

1. Shevchenko, S. et al., "The nature of lignin from steam explosion/enzymatic hydrolysis of hardwood," Applied Biochemistry and Biotechnology (1999) 77-79:867
2. Lu et al., "Cellulase Adsorption and an Evaluation of Enzyme Recycle During Hydrolysis of Steam-Exploded Softwood Residues," Applied Biochemistry and Biotechnology (2002) 98-100:641
3. Gama, F. and Mota, M., "Enzymatic hydrolysis of cellulose. 1. Relationship between kinetics and physico-chemical parameters," Biocatalysis and Biotransformation (1997) 15(3):221
4. Zhao, H. et al., "Studying cellulose fiber structure by SEM, XRD, NMR and acid hydrolysis," Carbohydrate Polymers (2007) 68:235
5. WO07111605
6. Pan, X. et al., "Bioconversion of hybrid poplar to ethanol and co-products using an organosolv fractionation process: Optimization of process yields," Biotechnology and Bioengineering (2006) 94(5):851
7. Sewalt, V. et al., "Lignin impact on fiber degradation. 3. Reversal of inhibition of enzymatic hydrolysis by chemical modification of lignin and by additives," J. Agric. Food Chem. (1997) 45:1823
8. Kim, S. and Holtzapple, M., "Effect of structural features on enzyme digestibility of corn stover," Bioresource Technol. (2006) 97:583
9. Kaar, W. and Holtzapple, M., "Benefits from Tween during enzymic hydrolysis of corn stover," Biotechnol. Bioeng. (1998) 59:419
10. Erikkson, T. et al, "Mechanism of surfactant effect in enzymatic hydrolysis of lignocellulose," Enzyme and Microbial Technology (2002) 31:353
11. Kurakake, M. et al., "Pretreatment of bagasse by nonionic surfactant for the enzymatic hydrolysis," Bioresource Technol. (1994) 49:247
12. Börjesson et al. "Effect of polyethylene glycol) on enzymatic hydrolysis and adsorption of cellulase enzymes to pretreated lignocellulose," Enzyme and Microbial Technology (2007) 41: 186
13. Börjesson et al. "Enhanced enzymatic conversion of softwood lignocellulose by poly (ethylene glycol) addition," Enzyme and Microbial Technology (2007) 40:754
14. Palonen, H. et al., "Dynamic interaction of Trichoderma reesei cellobiohydrolases Cel6A and Cel7A and cellulose at equilibrium and during hydrolysis," Appl. Environ. Microbiol. (1999) 65:5229
15. WO2005/067531
16. Kristensen, J. et al., "Use of surface active additives in enzymatic hydrolysis of wheat straw lignocellulose," Enzyme and Microbial Technology (2007) 40:8888
17. Tabka, M. et al. in "Enzymatic saccharification of wheat straw for bioethanol prpduction by a combined cellulase xylanase and feruloyl esterase treatment," Enzyme and Microbial Technology (2006) 39:897
18. Vermette, P. and Meagher, L., "Interaction of phospholipid- and poly (ethylene glycol)-modified surfaces with biological systems: relation to physico-chemical properties and mechanisms" Colloids and Surfaces B: Biointerfaces (2003) 28:153
19. WO2006/056838
20. Dasari, R. and Berson, R., "The effect of particle size on hydrolysis reaction rates and rheological properties in cellulosic slurries," Applied Biochemistry and Biotechnology (2007), 137:289
21. WO 2007/009463
22. Adney, B. and Baker, J., Laboratory Analytical Procedure #006, "Measurement of cellulase activity", Aug. 12, 1996, the USA National Renewable Energy Laboratory (NREL)
23. Ghose, T. K. 1987. "Measurement of Cellulase Activities, "*Pure & Appl. Chem.* 59: 257-268
24. Lever, M. et al., "A new reaction for colorimetric determination of carbohydrates", 1972, Anal. Biochem. 47: 273
25. Himmel, M. E. et al., "Isolation and characterization of a 1,4-beta-D-glucan glucohydrolase from the yeast, *Torulopsis wickerhamii*", 1986, J. Biol. Chem. 261: 12948-12955
26. Venturi, L. L. et al., "Extracellular beta-D-glucosidase from Chaetomium thermophilum var. coprophilum: production, purification and some biochemical properties", 2002, J. Basic Microbiol. 42: 55-66
27. Bailey, M. J., et al., "Interlaboratory testing of methods for assay of xylanase activity," Journal of Biotechnology (1992), 23:257

The invention claimed is:
1. A method for liquefaction and saccharification of lignocellulosic biomass comprising the steps of:

providing the solid fraction of steam or liquid hot water pre-treated lignocellulosic biomass, and treating said solid fraction at >20% dry matter with an effective amount of one or more cellulytic enzymes at less than about 7 FPU (g DM)$^{-1}$ in the presence of an amount of PEG between about 0.005 and 0.015 g (g DM)$^{-1}$ wherein the solid fraction is subject to pre-hydrolysis prior to introduction of fermentive organisms for a simultaneous saccharification and fermentation process, and wherein the absolute improvement in hydrolysis yield from PEG treatment is at least about 10%.

2. The method of claim 1 wherein pre-hydrolysis is conducted for between 2 to 24 hours prior.

3. The method of claim 1 wherein enzymatic hydrolysis is conducted in a continuous or semi-continuous process.

4. The method of claim 1 wherein absolute improvement of hydrolysis yield from PEG treatment is at least about 12%.

5. The method of claim 1 wherein the concentration of PEG is about 0.010 g (g DM)$^{-1}$.

6. The method of claim 1 wherein the concentration of PEG is between about 0.010 g (g DM)$^{-1}$ and 0.015 g (g DM)$^{-1}$.

7. The method of claim 1 wherein simultaneous saccharification and fermentation is conducted in a separate vessel.

8. The method of claim 1 wherein the concentration of PEG is about 0.010 g (g DM)$^{-1}$ and wherein absolute improvement of hydrolysis yield from PEG treatment is about 16%.

9. The method of claim 1 wherein the concentration of PEG is between about 0.010 g (g DM)$^{-1}$ and 0.015 g (g DM)$^{-1}$ and wherein cellulytic enzyme activity is added at between about 3-6 FPU (g DM)$^{-1}$.

10. The method of claim 1 wherein pre-treated biomass is introduced in a relatively continuous manner to pre-hydrolysis in a pre-hydrolysis unit which provides means for conveying biomass further into a communicating fermentation unit.

11. The method of claim 1 wherein pre-hydrolysis is conducted by combined enzymatic hydrolysis and mixing using free-fall mixing.

12. The method of claim 1 wherein PEG is PEG 6000, PEG 4000, PEG 2000, or PEG 1500 or any combination thereof.

13. The method of claim 1 wherein the lignocellulosic biomass comprises any one or any combination of corn stover, wheat straw, rice straw, bagasse, corn fiber, hardwood bulk, softwood bulk, nut shells, corn cobs, grasses, including coastal Bermuda grass and switch grass, paper, including newspaper, waste papers and paper from chemical pulps, sorted refuse, or cotton seed hairs.

14. The method of claim 1 wherein the solid fraction of a pre-treated lignocellulosic biomass comprises at least about 2.5 kg.

15. The method of claim 1 further comprising treating the solid fraction of a pre-treated lignocellulosic biomass with an effective amount of one or more xylanase enzymes.

16. The method of claim 15 wherein the concentration of PEG is between 0.010 and 0.015 g (g DM)$^{-1}$ and xylanase activity is added at between about 1000-5000 nkat (g DM)$^{-1}$.

17. The method of claim 16 wherein as a result of xylanase activity, xylan conversion is at least 10% higher in the presence of PEG relative to xylan conversion in the absence of PEG or surfactant.

18. The method of claim 15 wherein as a result of xylanase activity, xylan conversion is at least 16% higher in the presence of PEG relative to xylan conversion in the absence of PEG or surfactant.

19. The method of claim 15 wherein the solid fraction of a pre-treated lignocellulosic biomass comprises at least about 2.5 kg.

* * * * *